Figure 1:
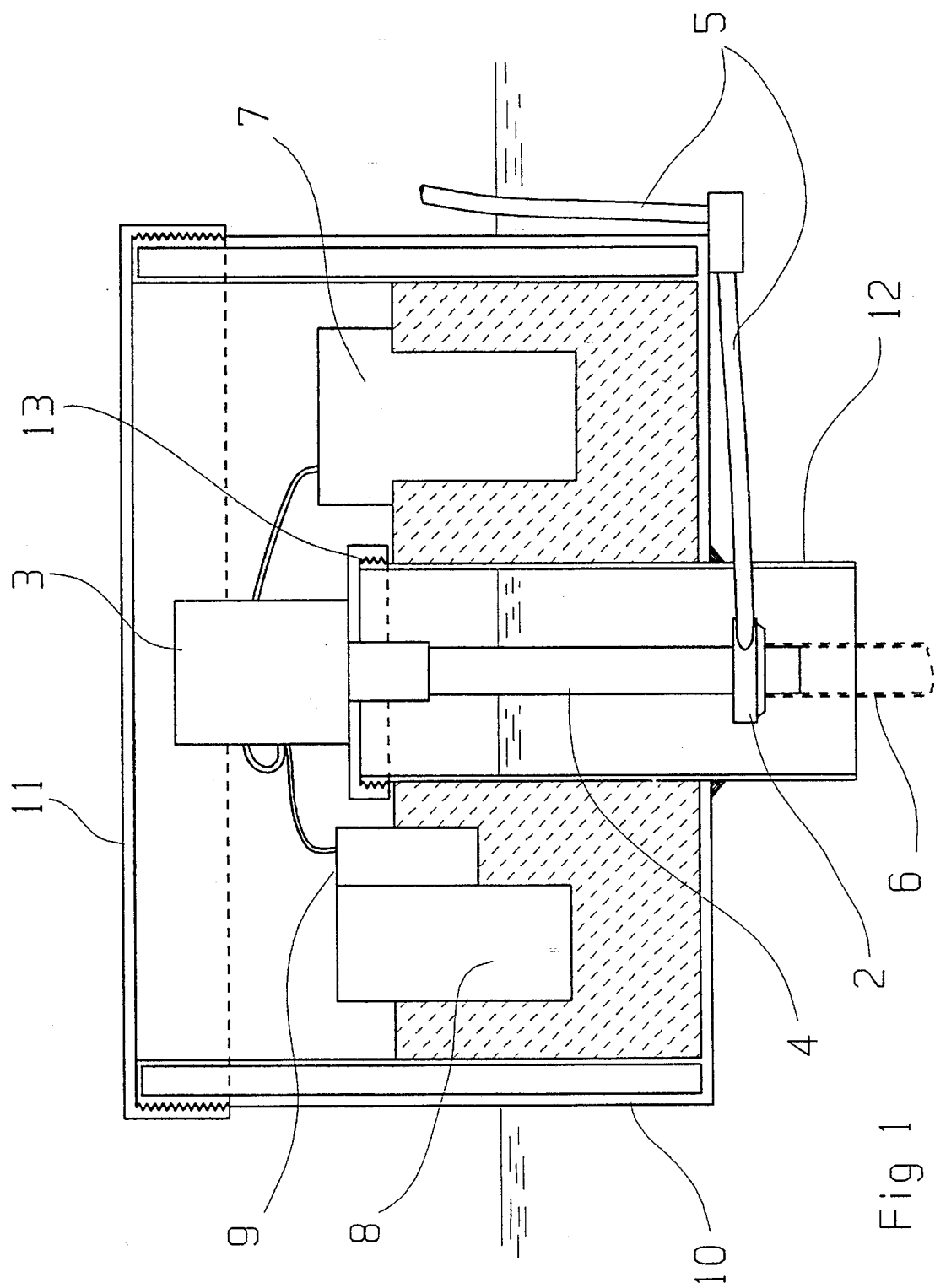

United States Patent [19]
Saarenketo

[11] Patent Number: 5,606,138
[45] Date of Patent: Feb. 25, 1997

[54] APPARATUS FOR WATER SAMPLING

[75] Inventor: Tapio Saarenketo, Rovaniemi, Finland

[73] Assignee: Tapio Saarenketo Oy, Finland

[21] Appl. No.: 464,741

[22] PCT Filed: Dec. 31, 1993

[86] PCT No.: PCT/FI93/00576

§ 371 Date: Aug. 14, 1995

§ 102(e) Date: Aug. 14, 1995

[87] PCT Pub. No.: WO94/16306

PCT Pub. Date: Jul. 21, 1994

[30] Foreign Application Priority Data

Jan. 5, 1993 [FI] Finland ................................ 930020

[51] Int. Cl.$^6$ ........................................................ G01N 1/14
[52] U.S. Cl. ................................................................ 73/864.34
[58] Field of Search ............................. 73/863.83, 863.84, 73/864.34, 864.35, 863.01, 864.73, 864.51

[56] References Cited

U.S. PATENT DOCUMENTS

| | | | |
|---|---|---|---|
| 2,841,012 | 7/1958 | Romer | 73/421 |
| 2,872,818 | 2/1959 | Johnson | 73/863.01 |
| 3,349,624 | 6/1965 | Fraga | 73/421 |
| 4,056,982 | 11/1977 | Jones | 73/864.34 |
| 4,462,265 | 7/1984 | Rein | 73/863.72 |
| 4,660,422 | 4/1987 | Eads et al. | 73/864.34 |

*Primary Examiner*—Robert Raevis
*Attorney, Agent, or Firm*—Nath & Associates; Gary M. Nath; Suet M. Chong

[57] ABSTRACT

The invention relates to an apparatus for water sampling. The invention relates to such a water sampling apparatus that permits intake of so-called composite samples as well as individual samples from different depths of water. The apparatus comprises a sampler (2) driven by an electric motor (3) and placed into connection with a buoyant container (10). The sampler is preferably a centrifugal pump (2) placed into connection with the container (10). The suction side of the pump (2) communicates with the sampling point and the pressure side communicates with a sample receiver. The sampler (2) is arranged to operate under control of a control unit (8) for taking samples of specific volume at specific intervals. The control unit (8) is placed inside said container (10). The electric motor (3) is powered by an accumulator (7) placed preferably inside the container (10).

5 Claims, 2 Drawing Sheets

APPARATUS FOR WATER SAMPLING

The invention relates to an apparatus for water sampling. The invention relates to such a water sampling apparatus that permits intake of so-called composite samples as well as individual samples from different depths. A composite sample denotes a sample which has been acquired by taking a small water sample e.g. at one hour intervals for one day into a sample receiver where the samples are mixed and wherefrom the actual water sample is taken for the desired water analyses. Composite samples are needed particularly in monitoring of the quality of natural waters and in monitoring and control of the operation of a water purification plants.

The patent publication U.S. Pat No. 4,462,265 discloses a system wherein a mechanical power unit lowered deep in the water is towed by a ship moving on the surface, the unit having a pump to pump water up. The water flows through several collection devices placed in series at various depths between the unit and the ship. The pressure of this water flow is adjusted by means of a throttle on the ship to a value high enough to actuate the valves of the collection devices and thereby permit the water samples in them to be conducted up to the ship. The pump gets its driving power from the towing movement of the ship by means of a turbine. The water sampling apparatus is large and is intended for moving and manned sampling from great and deep water systems.

Water samples are still collected so that the sample collecting person goes to the monitoring site at certain intervals to take a small sample into the collecting container. Sampling itself does not generally take much time so that the sampling costs are primarily made up of wage and travelling costs. Sampling devices operating on the piston principle are available. Since this kind of device needs a voltage of 220 V, it is difficult to install in terrain circumstances. The device also comprises a glass hoisting device which is heavy and breaks easily. The device is very expensive and therefore its use has remained limited.

The patent publication U.S. Pat. No. 4,462,265 discloses a system wherein a mechanical power unit lowered deep in the water is towed by a ship moving on the surface, the unit having a pump to pump water up. The water flows through several collection devices placed in series at various depths between the unit and the ship. The pressure of this water flow is adjusted by means of a throttle on the ship to a value high enough to actuate the valves of the collection devices and thereby permit the water samples in them to be conducted up to the ship. The pump gets its driving power from the towing movement of the ship by means of a turbine. The water sampling apparatus is large and is intended for moving and manned sampling from great and deep water systems.

The objective of the invention is to present an apparatus that allows automatic water sampling without the need for a continuous manning of the monitoring site. A further objective is a sampling apparatus which is small and moderate-priced. These objectives are obtained by means of an apparatus which is primarily characterized in what is presented in the characterizing part of claim 1.

In the apparatus according to the invention the sampler is a pump which is driven by an electric motor and which is placed into connection with a buoyant container. The apparatus is powered by an accumulator so that electric power lines are not needed at the sampling site as in the case of prior art apparatuses. Because the apparatus is cheap on one hand and easy to transport on the other hand, sampling apparatuses needed in several monitoring sites can be installed in one go and also the samples can be collected in one go.

Figure 2:
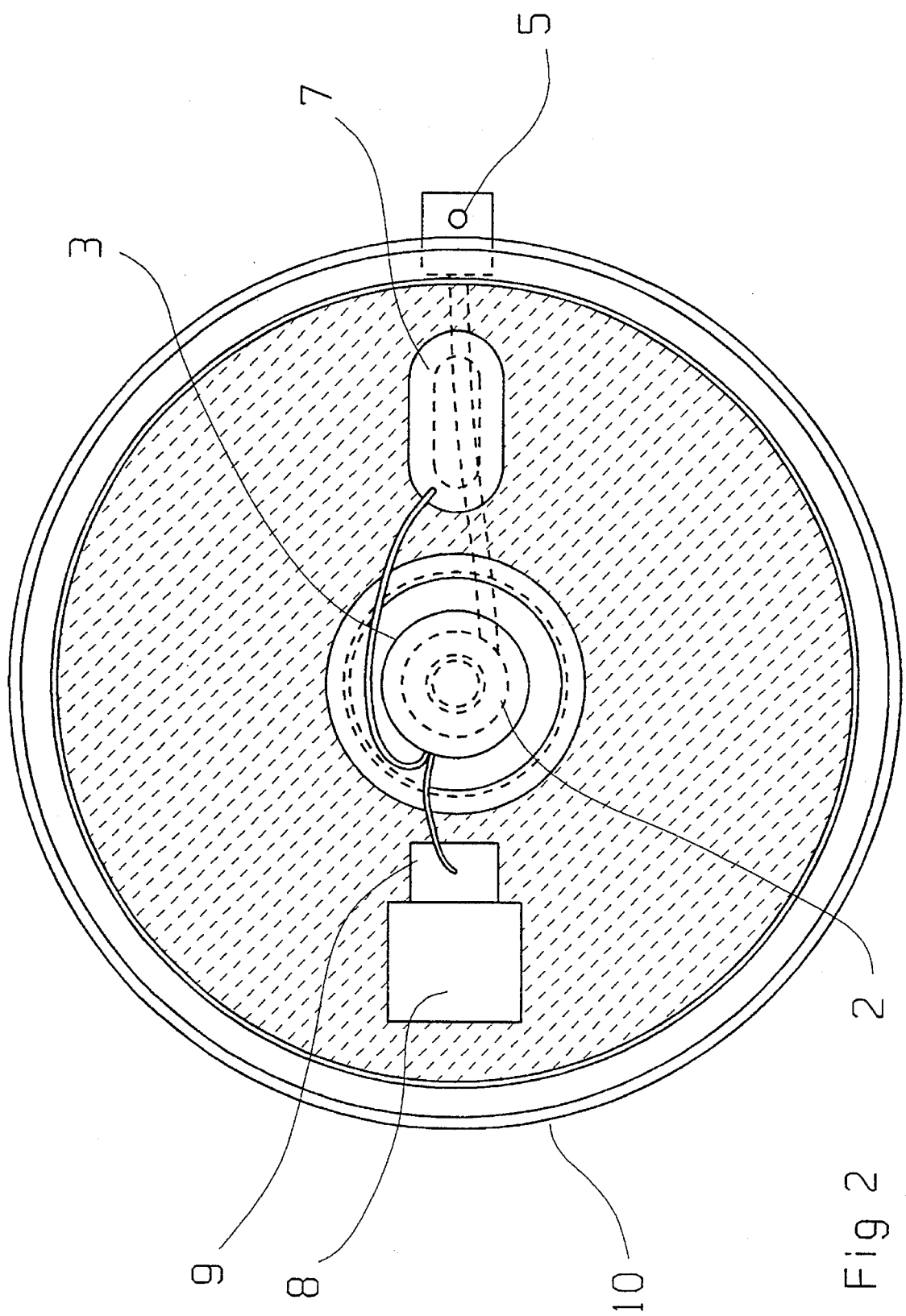

The invention will be described in greater detail in the following referring to the enclosed drawings in which FIG. 1 shows a vertical cross-section of the apparatus and FIG. 2 shows a horizontal cross-section of the apparatus.

The apparatus according to the invention consists of a buoyant sampling device 2 driven by an electric motor 3. In the exemplary case the sampling device 2 is a centrifugal pump which is mounted to a sealed, buoyant container 10. The container 10 is, in the exemplary case, made of plastic. Pump 2 is placed so that its suction side communicates with the sampling point and the pressure side communicates with the sample receiver (not shown in the figures) e.g. by means of hoses. In the exemplary case, container 10 also accommodates other equipment which are needed in the sampling operation.

The buoyancy of container 10 is accomplished by the vessel-like or casing-like structure and the fact that the lower part of container 10 is filled with a material like polystyrene, for example, which is lighter than water. The walls of the container may also be provided with air-filled cavities. Container 10 has a tightly closing cover 11. A tubular part 12 in the middle of container 10 leading through the bottom of the container is welded to the bottom of container 10. The tubular part 12 is placed so that its first end i.e. the upper end extends approximately to the middle of container 10 and its second end i.e. the lower end slightly below the bottom of container 10. Both ends of the tubular part 12 are open. The first end of the tubular part is provided with threads 13.

The sampling device 2 is driven by a motor 3. In the exemplary case, motor 3 is fastened in position onto the first end of the tubular part 12 by means of threads 13. Motor 3 is above the tubular part 12 and it closes watertightly the first end of the tubular part 12 i.e the upper end.

Motor 3 and the sampling device 2 are placed into connection with the tubular part 12 so that the shaft 4 of motor 3 which drives pump 2 is inside the tubular part 12. The length of shaft 4 is such that pump 2 is located slightly below the bottom of container 10 at the second end of the tubular part 12. When the apparatus is placed in position for sampling, the tubular part 12 becomes at least partly filled with water. Pump 2 is placed so that the water sample can be taken from a flowing water right below the apparatus or from a desired depth by means of an extension tube connected to the suction opening of pump 2. Because in the apparatus according to the invention the suction side of pump 2 is in continuously communicating with the water which is being sampled, no air can accumulate in the apparatus which would interfere with sampling.

A tube 5 leads from pump 2 to the sample receiver which can be a separate watertight container which floats on water. The sample receiver can also be placed farther or higher from the actual sampling apparatus.

If it is desired to use the apparatus for sampling at greater depths, a tube 6 can be attached to the suction opening of the pump whereby samples can be collected from a desired depth below container 10. If the apparatus is used for collecting samples from various depths, tube 6 is lowered to the desired depth and the first sample is extracted into the container. Tube 6 is then lowered for a desired distance and the second sample is extracted into the container in this case, the apparatus must be operated so that the water in the tube is first conducted past the container before the actual water sample is taken from the desired depth. When the samples have been collected, tube 6 is lifted manually or by a specific winch (not shown in figures).

The electric motor 3 driving pump 2 is powered by an accumulator. Accumulator 7 is placed inside container 10 to the bottom thereof. Accumulator 7 can be a 12 V battery generally used in battery-driven drilling machines. Container 10 also accommodates a control unit 8, e.g. a timer, and a relay 9 for controlling the operation of the electric motor 3 and pump 2. By means of timer 8, pump 2 can be programmed to pump water at specific intervals and the length of the run time of pump 2 can also be adjusted. Timer 8 is preferably of the kind that allows stepless control. The length of the run time of pump 2 is adjusted to a suitable value depending on the volume of water needed and the power of the pump. For a composite sample only about 20 cl of water is needed for an individual sample at a time. It takes only 2–3 seconds to pump this quantity of water.

The equipment needed for the control and driving of pump 2 can be naturally placed also outside the apparatus. This can be done particularly in the case when the intention is to vary the sample volume or the sampling rate during the collection operation.

In addition to composite samples the apparatus enables collection of so-called undisturbed individual samples from different water depths. Samples can be taken in vertical direction at arbitrary depths by lowering the tube connected to the suction side of the pump. By means of the apparatus it is possible to localize accurately in vertical direction e.g. water layers with low oxygen content and observe in vertical direction other changes which affect the water quality. For example, the apparatus greatly facilitates following of narrow waste water zones which move underwater.

The invention is not limited to the above embodiments but it can be varied within the limits of the enclosed claims. Therefore, the sampler can also be a membrane pump or a peristaltic pump.

I claim:
1. A buoyant apparatus for water sampling comprising:
 (a) buoyant container (10) capable of being closed watertightly;
 (b) in said container, an electric motor (3) and a battery (7) for supplying power to said electric motor;
 (c) a pump (2) mounted to said container and driven by said electric motor, said pump having a suction side and a pressure side;
 (d) connected to the suction side of said pump, means (6) for communicating with a sampling point;
 (e) connected to the pressure side of said pump, means (5) for communicating with a sample receiver; and
 (f) in the container, a control unit (8) controlling the operation of said electric motor;
wherein said control unit (8) is programmable to run said electric motor (3) and pump (2) during certain run times at specific intervals for taking samples.

2. Apparatus according to claim 1, wherein the pump (2) is a centrifugal pump.

3. Apparatus according to claim 1, wherein the pump (2) is placed inside a tubular part (12) which opens to the bottom of the container (10).

4. Apparatus according to claim 1, wherein the electric motor (3) is attached to the upper part of the tubular part (12) and the pump (2) is mounted on the shaft of the electric motor (3) inside the tubular part (12).

5. Apparatus according to claim 1, wherein the means communicating with the sampling point includes a tube (6) the mouth of which can be lowered to a desired depth for taking a water sample.

* * * * *